United States Patent [19]
Sliwa, Jr. et al.

[11] Patent Number: 5,690,113
[45] Date of Patent: Nov. 25, 1997

[54] METHOD AND APPARATUS FOR TWO DIMENSIONAL ULTRASONIC IMAGING

[75] Inventors: John William Sliwa, Jr., Los Altos; Stacey T. Baba, Saratoga, both of Calif.

[73] Assignee: Acuson Corporation, Mountain View, Calif.

[21] Appl. No.: 664,126

[22] Filed: Jun. 14, 1996

[51] Int. Cl.$^6$ .................................................. A61B 8/00
[52] U.S. Cl. ............................... 128/660.07; 128/916
[58] Field of Search ............ 128/660.01, 660.04–660.05, 128/660.07, 661.01, 661.09–661.1, 916; 364/413.25

[56] References Cited

U.S. PATENT DOCUMENTS

| | | | |
|---|---|---|---|
| 3,086,390 | 4/1963 | Brown | 128/660.09 |
| 3,777,140 | 12/1973 | Hokanson | 128/661.09 |
| 4,058,001 | 11/1977 | Waxman | 128/660.07 |
| 4,100,916 | 7/1978 | King | 128/416 X |
| 4,431,007 | 2/1984 | Amazeen et al. | 128/660.04 |
| 4,534,221 | 8/1985 | Fife et al. | 128/661.01 X |
| 4,821,731 | 4/1989 | Martinelli et al. | 128/660.03 X |
| 5,078,145 | 1/1992 | Furuhata | 128/916 X |
| 5,295,486 | 3/1994 | Wollschlögen et al. | 128/916 X |
| 5,315,512 | 5/1994 | Roth | 364/413.25 |
| 5,329,929 | 7/1994 | Sato et al. | 128/916 X |
| 5,353,354 | 10/1994 | Keller et al. | 364/413.25 X |
| 5,394,875 | 3/1995 | Lewis et al. | 128/916 X |
| 5,505,204 | 4/1996 | Picot et al. | 128/661.1 |
| 5,529,070 | 6/1996 | Augustine et al. | 128/916 X |
| 5,540,229 | 7/1996 | Collet-Billon et al. | 128/916 X |
| 5,608,849 | 3/1997 | King, Jr. | 128/660.07 X |

OTHER PUBLICATIONS

Leotta, D. et al., "Three–Dimensional Ultrasound Imaging Using Multiple Magnetic Tracking Systems and Miniature Magnetic Sensors," University of Washington, Seattle, (4 pages, date unknown).

Raab, R. et al., "Magnetic Position and Orientation Tracking System," IEEE Transactions on Aerospace and Electronic Systems, vol. AES–15, No. 5, pp. 709–718, Sep. 1979.

Detmer, P. et al., "3D Ultrasonic Image Feature Localization Based On Magnetic Scanhead Tracking: In Vitro Calibration and Validation," Ultrasound in Med. & Brol., vol. 20, No. 9, pp. 923–926, 1994.

Product Brochure from Ascension Technology Corp., "Flock of Birds," (2 pages, date unknown).

Primary Examiner—Francis Jaworski
Attorney, Agent, or Firm—Brinks Hofer Gilson & Lione

[57] ABSTRACT

A method and device for ultrasonically imaging a body that includes a movable ultrasonic transducer capable of imaging a scanline wherein the scanline is fixed in orientation and spatial position relative to the movable transducer. The device contains a means for sensing transducer position information wherein the sensing means is in communication with an ultrasound console. A computing means computes the spatial position and the orientation of each scanline as the transducer is moved. The scanlines are then presented as a complete image. Alternatively, an electromagnetic transmitter and receiving sensor determine the spatial orientation and position of each scanline in free space. The method of generating a two dimensional ultrasonic image is also disclosed.

16 Claims, 2 Drawing Sheets

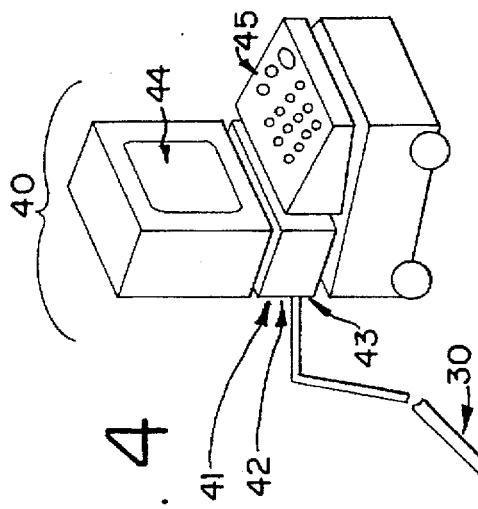
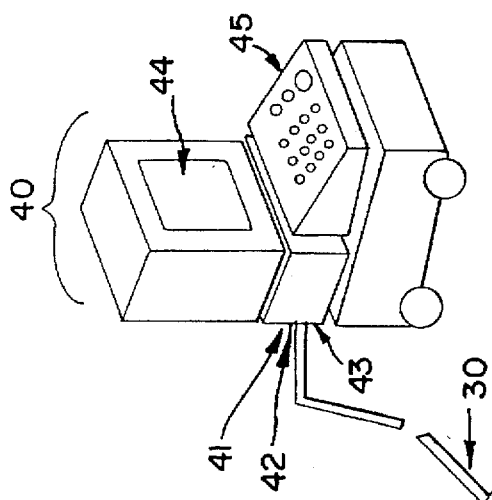
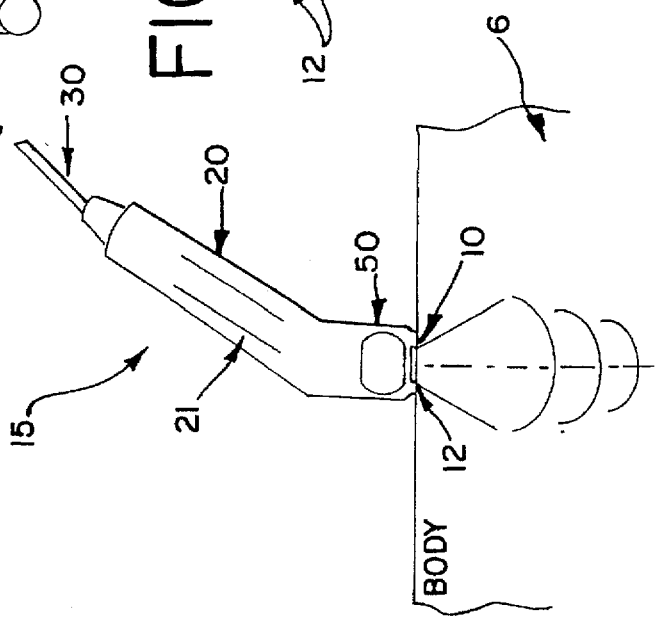

METHOD AND APPARATUS FOR TWO DIMENSIONAL ULTRASONIC IMAGING

FIELD OF THE INVENTION

The present invention generally relates to a method and apparatus for ultrasonic imaging, and more particularly to a method and apparatus for generating a two dimensional ultrasonic image using a hand-held single element transducer probe having a fixed scanline.

DESCRIPTION OF THE RELATED ART

Brightness scan (B-scan) or B-mode modulation is one type of ultrasonic scanning that results in a two dimensional cross-sectional display of reflecting structures within a body. In B-mode modulation, reflecting structures are represented by bright areas on a display. The brightness of the reflecting structure or structures is primarily dependant on tissue impedance variations. Gain controls on the system may be adjusted with depth such that equivalent tissue features have similar brightness regardless of depth.

FIG. 1 shows a prior art ultrasonic system 1 of an articulated or mechanically positioned arm-mounted B-mode transducer type. Such a system includes an encoder positioning device 2A, an echo data acquisition device 2B, a linked mechanical arm 3, position encoders 4A, 4B, 4C and a single element transducer probe 5. This prior art system generates an ultrasonic image formed of a plurality of scanlines created by manually sweeping the probe 5 over a body 6. The body 6 can either be an exterior body surface or a surface of internal organs or tissue examined during an intraoperative or endocavity procedure.

The probe 5 contains a single element piezoelectric material which sends a scanline or sound wave into the body 6. To perform a sonogram, the transducer 5 is manually manipulated to sweep or scan the body 6. The sound waves generated by the probe penetrate into the body 6 and reflect off of structures within the body 6. These waves are reflected back to the probe 5 and this information is sent to the echo acquisition device 2B in the form of individual scanlines.

The mechanical arm 3 assists in determining the transducer probe 5 location and therefore the location of each individual returned echo or scanline in free space. More particularly position encoders 4A, 4B and 4C attached to the mechanical arm 3 sense the angles $\theta_1$, $\theta_2$, and $\theta_3$, respectively and send this information to the encoder positioning device 2A. The transducer probe 5 is physically attached to the mechanical arm 3 by a linking or attaching means.

As the sonographer manually sweeps or scans body 6 scanline by scanline, an image of a cross section generally perpendicular to the examined body surface is generated. The system 1 gathers scanline data and the position and orientation of each scanline is computed and assigned to each scanline based on the encoder angles. With respect to FIG. 1, encoders 4A, 4B and 4C located at the joints in arm 3 generate the positional components of each individual scanline's position and orientation in the X and Y directions. Additional encoders and joints may be employed to enable transducer probe motion in the Z direction or to enable the transducer to be rotated during scanning.

There are several disadvantages associated with articulated or mechanically positioned arm-mounted transducer systems such as that in FIG. 1. One disadvantage is that they are mechanically complex and bulky. Contact between the transducer and the area being scanned is difficult to achieve with mechanical probes because of the arm's poor mobility and interference. This further complicates obtaining internal sonograms. Additional encoders and arm joints increasingly restrict the maneuverability of the probe thereby adding to the overall system complexity.

Poor probe mobility also makes it difficult to use tissue marking systems in conjunction with these prior art mechanical systems. Marking systems enable the sonographer to locate and mark areas of interest during a sonographic examination. They also enable the surgeon to know with precision what underlies an intended incision line. The location, identification and marking of areas of interest such as intended incision lines is therefore further complicated.

As mechanical probes are used for both external and internal body sonograms, they must be sterilized prior to each use. The mechanical nature of these prior art devices complicates this requirement. To diminish these problems somewhat, a disposable "rubberbooty" or condom is slipped or placed over the probe 5. Although the disposable booty provides adequate sterilization enabling multiple probe use, it diminishes body surface-to-probe contact and requires an extra system cost. Prior art probes which do not require a latex rubber-booty to insure sterility must be built reliably enough so that the probe can withstand multiple sterilizations which also increases the cost of such systems and slows patient throughput.

Aside from articulated or mechanical arm transducers such as that of FIG. 1 which use an annular array or a single piezoelectric element, there are transducers which consist of an angularly swept single piezoelement in an otherwise stationary handheld probe body. Because of the pivoted piezoelement motion, the image format is sector shaped. The single scanline is thus mechanically swept to form a 2D "sector" image.

Mechanical sector array probes, however, have a number of disadvantages. For example, because of the heavy weight of the probe housing, mechanical sector array probes cause fatigue to the user of the probe during sonograms. In addition, sector array probes exhibit poor mechanical reliability resulting in frequent probe failure.

Another prior art device is the phased array transducer probe. A phased array transducer includes a plurality of transducer elements formed of piezoelectric material arranged in an array. Each transducer array element is controlled individually with a delay line and can be fired or connected in rapid sequence. The staggered firing of the array elements produces steered scanlines, thereby allowing for electronic scanline steering rather than mechanical steering.

One disadvantage with phased array devices is their expensive fabrication. These devices also require sophisticated software and hardware to support operation, particularly when real-time high frame rate beamforming is required.

Phased array devices also generally require a large cable to communicate with the many piezoelements of the array. The size of the cable varies proportionally to the number of elements contained in the phase array. For example, a phase array probe having 128 elements typically requires a cable containing 128 wires, one wire for each element. Therefore, the greater the number of phased array elements, the greater the probe immobility due to the increased cable size and the greater the overall system cost.

There is, therefore, a need for a reliable, easily maneuverable, inexpensive, portable, two dimensional ultrasonic device, which can be manipulated without the restrictions associated with a mechanical interconnecting arm or a bulky cable. There is also a need for a cost-effective disposable probe which does not require a latex rubber booty or condom for sterilization.

There is a further need to allow the examining sonographer to make easier contact between the probe and the body surface during an examination. There is also a need to reduce a sonographer's fatigue due to the excessive weight and immobility associated with mechanical probes.

It is also desirable to provide a transducer probe having a small footprint to facilitate the intimate positioning, sweeping or tilting of the probe. Such a transducer probe makes it easy to examine or scan areas of a body that are not easily accessible. In addition, the small footprint allows imaging of curved or noncontinuous planes.

There is a further need for a fixed scanline transducer probe containing a single element or a multiple element annular array. A device having a limited number of piezoelectric elements does not require complex beamforming or beamsteering circuitry. Such a probe with a fixed scanline could be dragged across the tissue. By integrating a non-obtrusive position encoder means one could gather the 2D images of the device of FIG. 1 without the complexity. Such a device would be considerably less expensive than a phased array.

There is a further need for an ultrasonic system where the probe is used in conjunction with a tissue marking system, enabling the probe user to locate and mark areas of interest. There is a further need to provide the sonographer with two dimensional images along intended surgical incisions.

SUMMARY OF THE INVENTION

A device and method for two dimensional ultrasonic imaging for a body is disclosed. According to a first aspect of the present invention, the device includes a probe containing an ultrasonic transducer. The transducer is capable of imaging a single scanline wherein the scanline is fixed in orientation and spatial position relative to the probe body during scanning. The transducer has at least one piezoelement capable of transmitting and receiving along the fixed scanline. Ultrasound electronics are in communication with the probe and transmit and receive ultrasound along the fixed scanline. The device contains a means for tracking the spatial position and orientation of the probe such that the spatial address of every scanline contributing to the image is known. Receiving means in communication with the probe receive the reflected acoustic signals along the scanline. Transmitting means in communication with the probe transmit ultrasound into the body also along the scanline. The spatial position and the orientation of each scanline is computed by a computing means based on inputs from the tracking means and the triggering times of the scanline datasets. The scanlines are then presented as a complete image using the individual spatial addresses of the scanlines to properly locate the scanlines in relation to each other on the display.

In another aspect of the present invention, an electromagnetic transmitter and receiving sensor determine the spatial orientation and position of each scanline in free space. It will be obvious to those familiar with position trackers, including the compact non-obtrusive electromagnetic tracker system of this invention, that one may simply report the positions of the scanline samples or may choose to trigger scanline samples based on the position data. The latter method can assure proper scanline coverage of a tissue region-of-interest despite a wide variety of probe motions.

The invention itself, together with further objects and attendant advantages, will best be understood by reference to the following detailed description, taken in conjunction with the accompanying drawings.

BRIEF DESCRIPTION OF THE DRAWINGS

FIG. 3 illustrates a multi-element single scanline transducer probe ultrasonic system according to a preferred embodiment of the present invention.

FIG. 3A illustrates the multi-element single scanline transducer probe configuration of the ultrasonic system shown in FIG. 3 of the present invention.

FIG. 4 illustrates an ultrasonic system according to another preferred embodiment of the present invention.

DETAILED DESCRIPTION OF THE PRESENTLY PREFERRED EMBODIMENTS OF THE PRESENT INVENTION

Figure 1:
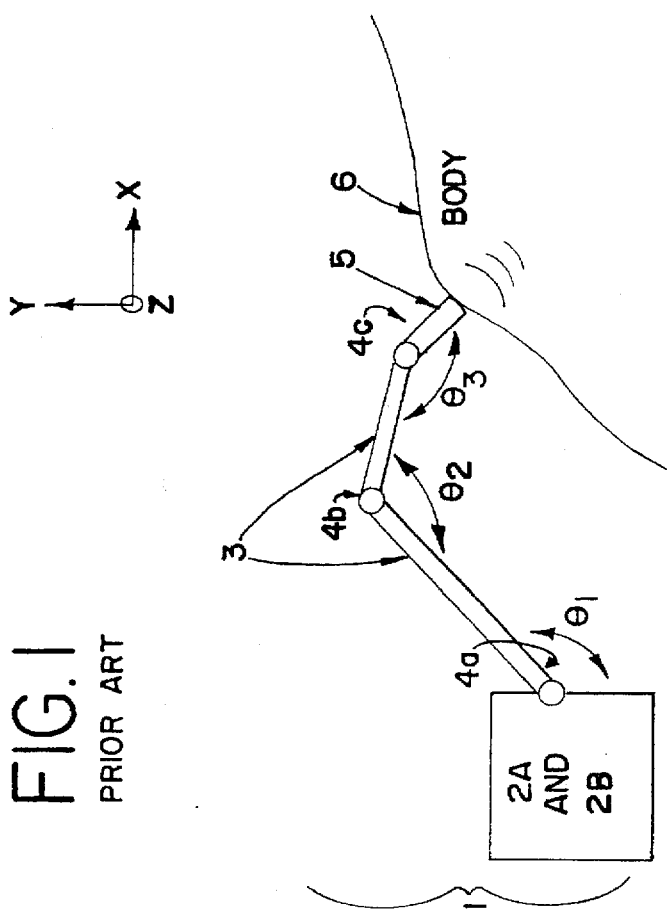
FIG. 1 is a diagram of an ultrasonic system utilizing a prior art mechanically linked single element transducer probe.
Figure 2:
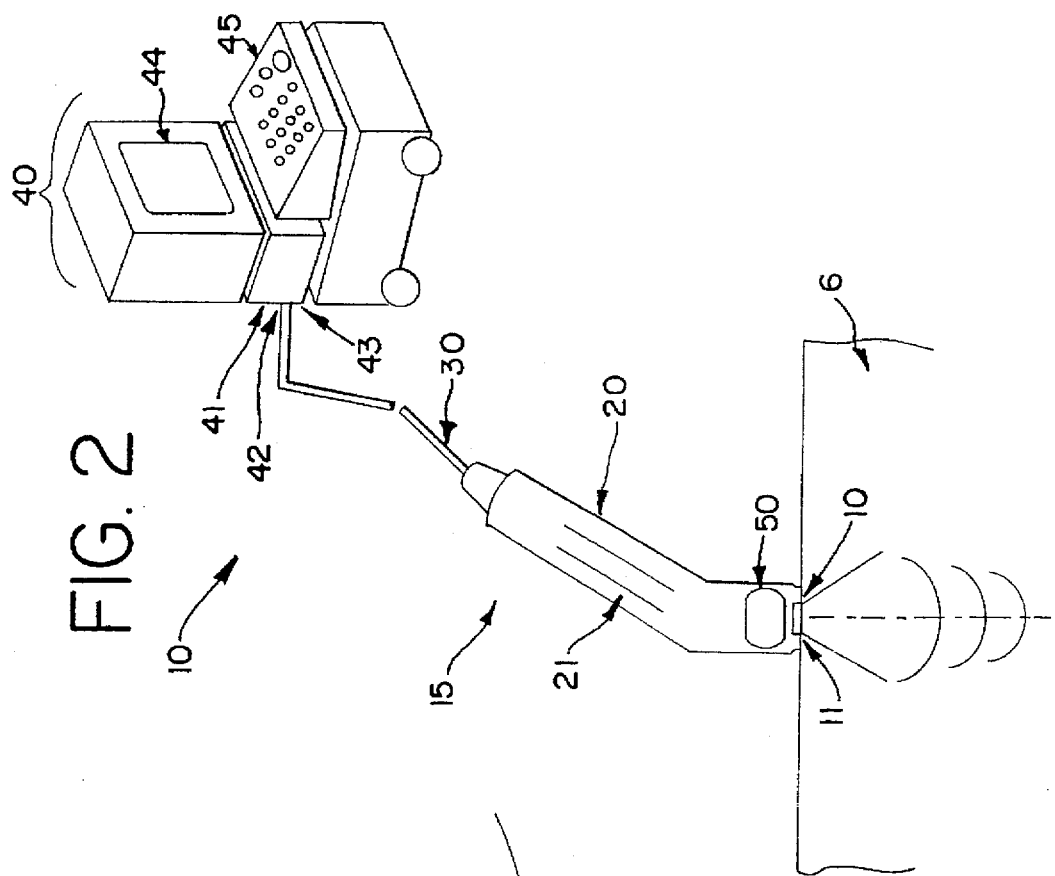
FIG. 2 illustrates a single element single scanline transducer probe ultrasonic system according to a preferred embodiment of the present invention.

FIG. 2 illustrates an ultrasonic system according to a preferred embodiment of the present invention. The ultrasonic system 10 includes an ultrasonic probe 15, an ultrasound console 40 and a cable 30 coupling the probe 15 and console 40. The probe 15 includes an ultrasonic transducer 10, an electromagnetic positioning sensor 50, and a probe case 20. In this preferred embodiment, the ultrasonic transducer 15 includes at least one piezoelement 11. In a preferred embodiment, the single piezoelement 11 is either a single concave or a single convex circular piezoelectric element. When an electrical pulse is applied to the piezoelement 11, its shape is altered and consequently generates a small pressure wave along a scanline 99 which is pulsed into the body 6. The returned or reflected pressure wave, along with its orientation and position coordinates, all of which define a scanline in relation to body 6, is communicated to the ultrasound console 40 for processing and imaging. As probe 15 is moved multiple such scanlines 99 "paint" an image on the console display 44.

The piezoelement 11 is contained or enclosed in a probe case 20. Because the probe 15 must be sterile before each use, the probe case 20 is preferably a lightweight, heavy duty material such that it can withstand multiple sterilizations. Alternatively, the probe case 20 can be an inexpensive lightweight material so that the probe 15 can be disposed of after each use.

FIG. 3 illustrates a multi-element single scanline transducer probe ultrasonic system according to another preferred embodiment of the present invention. Like reference numerals will be used for like components. In this alternative embodiment, the ultrasonic transducer 10 is a multi-element annular array 12. FIG. 3A illustrates a surface of the multi-element array shown in FIG. 3. The array 12 shown has three concentric elements for viewing along scanline 99.

Returning to the preferred embodiment shown in FIG. 2, a single transducer element 11 such as a single concave circular element or an annular array is used. Such single transducer elements provide an enhanced image resolution in the elevation dimension compared to that which can be achieved using a phased array since element 10 focuses in all axes perpendicular to scanline 99. Both the single concave or circular element and annular array are capable of generating a highly focused scanline with a lateral resolution in all axes much better than the lens-focussed elevation resolution of a phased array.

Preferably, the probe case 20 is designed to assist the user's handling of the probe 15 by providing grip detail 21. The grip detail 21 may consist of ridges, indentations, dimples or small raised dots, and aides in the freehand operation of the probe 15 during scanning of the body 6.

The probe 15 is coupled to and in communication with an ultrasound console 40. Because the preferred embodiment shown in FIG. 2 has only one piezoelement, or concentric annular array requiring just a few wires, for example 1 for the transducer element of FIG. 2 and 3 for the transducer element of FIG. 3A, the size of the cable 30 is much smaller than prior art phased array devices. The reduced cable size substantially improves the probe's 15 maneuverability.

The scanline information generated by the probe 15 is communicated to the ultrasonic console 40. Preferably, the ultrasound console 40 includes a data acquisition system 41, an electromagnetic positioning transmitter 42 and an electromagnetic positioning computer 43. Scanline information and position information are transmitted from the probe 15 to the console 40. Alternative untethered means of communicating may also be used, including radio or infrared communication.

In the preferred system 10, the transducer positioning is preferably provided using a magnetic spatial positioning system as provided by either Ascension Inc. or Polhemus Inc., both of Burlington, Vt. Both products have a microcomputer box (optionally integratable in 40 as shown) which controls all electronic and software functions related to determining position, a multicoil magnetic field transmitter also integratable in 40 if desired, and position tracking, receiving sensors 50 for probe 15.

The ultrasound console 40 will typically have a video display screen 44 and a keyboard 45. The screen 44 collectively displays the acquired scanline image data sent via the cable 30 from the probe 15 to the data acquisition system 41. The keyboard 45 is used for controlling the overall system 10 and for processing the imaging information stored in the data acquisition system 41.

In an alternative embodiment the multicoil magnetic positioning transmitter may be placed in proximity to the patients body 6 rather than in console 40.

Preferably, the position receiving sensor 50 is contained in or attached to the probe case 20. The electromagnetic position receiving sensor 50 and the electromagnetic position transmitter 42 work in conjunction with one another to electromagnetically determine the spacial orientation and position of each scanline in free space. For the transmitter 42 and sensor 50 to work effectively, the electromagnetic position transmitter 42 must be stationary relative to the desired reference system. In a typical application the transmitter need only be stationary relative to body 6.

The magnetic fields communicated from the transmitter 42 to the electromagnetic position receiving sensor 50 contain vector information relating to the position and orientation of the electromagnetic position receiving sensor 50 relative to the stationary electromagnetic position transmitter 42. Preferably, nine components of data or measurements are communicated and therefore available to solve for six unknowns: X, Y, Z for position; and azimuth ($\psi$), elevation ($\theta$) and roll ($\Phi$) for orientation. The raw sensed data is transmitted from the sensor 50 back to the positioning computer 43 where calculations are made to locate the ultrasonic probe 15 and hence each scanline in free space.

Preferably the receiving sensor 50, as stated, relies on magnetic spatial positioning which is non-contact and does not require line-of-sight sensing. As long as precautions are taken by limiting the amount and movement of metal objects in the vicinity of such electromagnetic positioners, they can be accurate to approximately 0.2 millimeters and 0.3 degrees. In addition, the receiving sensor 50 is passive in that it receives or senses the magnetic fields produced by the transmitter 42 but does not create them.

The electromagnetic position receiving sensor 50 is a preferred sensor for determining position data in the console 40 since it is an inexpensive, small, and lightweight position determining device. This also reduces the amount of fatigue experienced by the operator performing a sonogram. Also, because the sensor 50 itself is an inexpensive component of the magnetic position determining device, it allows the probe 15 to be optionally disposed of after each patient exam thereby eliminating the requirement for sterilization. One may arrange for position sensor 50 to clip onto probe 15 such that only probe 15 itself is disposable and the positioner 50 is reused.

The magnetic system including the sensor 50 and the transmitter 42 allows for the inexpensive determination of the location of the probe 15 and therefore of each scanline in free space. The magnetic sensor 50 senses the probing magnetic fields transmitted by the transmitter 42, optionally located in the console 40. The positioning computer 43 receives the real time sensed transmitter magnetic field components from the sensor 50 and assigns each returned scanline a spatial position. The data acquisition system 41 may store all the position data communicated to it. The Ascension magnetic system referred to is a preferred system because it has less interference from metallic objects, for example, a patient gurney in the field of sensed motion.

Preferably, both the electromagnetic position transmitter 42 and the electromagnetic position receiving sensor 50 are magnetic dipole antennas. Most preferably, the magnetic dipole antennas consist of three mutually orthogonal wound coils. Each coil of the electromagnetic position transmitter 42 is excited with a driving signal identical in frequency and phase. The electromagnetic position transmitter 42 excitation is therefore a pattern of three states, each state having three positioning elements. Exciting the electromagnetic position transmitter 42 generates outputs to the receiving sensor 50 resolvable as a set of three linearly independent vectors. These vectors are received by the electromagnetic position receiving sensor 50. Although magnetic positioning is the preferred approach to computing scanline location, alternative means for computing location may also be used.

For example, optical positioning systems such as those systems equipped with LEDs and photodetectors could be used as a means for positioning. These systems, however, depend upon line-of-sight. Therefore, extra sensors may be required to insure visibility and to obtain position information. This would preclude the use of such systems where access to the body is difficult or where line of sight positioning is difficult.

CCD video image positioning systems, another alternative method, requires at least one CCD video camera. This method is also dependent upon line of sight. Therefore, this would have the similar limitations as the optical positioning systems. In addition, this method is not as cost effective as the magnetic positioning systems.

Prior-art or future echo methods could also be used for positioning scanlines 99. With this type of system, an acoustic signal, usually audible, is transmitted from a device attached to or on the transducer and received by microphones in the corners of a room (or vice versa). The accuracy of this method is limited and errors can occur due to other audible signals present in the area. In addition, the constant audible signal emitted can be very irritating to the user over time.

Inertial sensing could also be used for scanline 99 positioning. This method requires inertial accelerometers and/or gyroscopes. Although this method is feasible, it is not as accurate as magnetic positioning systems due to drift instabilities.

Knowing the position of the probe 20, one can determine the position of the scanline 99 in space at that moment. Each scanline 99 is tagged with a unique spatial address. Preferably, this unique address is represented by the quantities $\psi$, $\theta$, $\Phi$, x, y, z and these refer to a reference point on or along scanline 99, such as the origin of scanline 99 and its orientation about that origin.

As long as the magnetic transmitter is placed in an environment whose movement is relatively static with relation to the movement of the probe 20, this system will function adequately.

FIG. 4 illustrates an ultrasonic system according to another preferred embodiment of the present invention. The ultrasonic system of FIG. 4 further includes a tissue marker 60. Preferably, this marker 60 is a tissue marking system in the form of a writing instrument coupled to the probe 15. Preferably, the marker 60 is attached to the probe 15. The marker 60 enables the marking of the area of interest such as an intended incision line on the body. The writing action of the marker may, for example, be triggered by a footpedal (not shown) in response to the image being displayed on display 44. The writing action may also be automatically triggered by the systems recognition of certain features, such as the presence of flow, in the image or a scanline.

The present invention therefore provides a lightweight, agile and inexpensive way of obtaining high quality ultrasound images while avoiding much of the cost and complexity of a system that requires beam steering electronics and/or software. The disclosed embodiments determine the spatial location and orientation of the probe without the disadvantages associated with such mechanical systems.

While several illustrative embodiments of the present invention have been shown and described, numerous variations and alternative embodiments will occur to those skilled in the art. Such variations and alternate embodiments are contemplated, and can be made without departing from the spirit and scope of the invention defined by the appended claims.

What is claimed is:

1. A non-real time ultrasonic imaging system for scanning a body the system comprising:

an untethered probe adapted for use on the exterior surface of the body and having an ultrasonic transducer, capable of transmitting signals and receiving signals along a scanline, wherein the scanline is fixed in orientation and unmovable with respect to the untethered probe;

ultrasound electronic in communication with the probe, the ultrasound electronics transmitting signals and receiving signals from the probe;

means on the probe for sensing position information relating to the scanline; and means in communication with the sensing means and coupled to the electronics for computing the spatial position and the orientation of the scanline relative to a coordinate system and transmitting the scanline orientation and spatial position to the electronics wherein the electronics identifies each scanline by a unique spatial address;

a memory coupled to the electronics for storing the addressed scanlines;

a display coupled to the memory and electronics for displaying an image generated by the electronics from the addressed scanlines, wherein the movement of the probe results in the accumulation of multiple spatially addressed scanlines displayable as an image in a scanplane.

2. The device of claim 1, further comprising a means for marking the location of the probe on the body being examined during examination, wherein the marking is triggered by one of user control or automatic system recognition of features of interest in the ultrasound data.

3. The device of claim 1, wherein the ultrasonic transducer has at least one single concave piezoelement.

4. The device of claim 3, wherein the piezoelement is circular in shape.

5. The device of claim 1, wherein the ultrasonic transducer is a multielement annular array.

6. The device of claim 1, wherein the ultrasonic transducer has at least one single convex piezoelement.

7. The device of claim 6, wherein the piezoelement is circular in shape.

8. A non-real time ultrasonic imaging system the system comprising:

a probe adapted for use on the exterior surface of the body and having an ultrasonic transducer, the transducer capable of imaging along a scanline, wherein the scanline is fixed in orientation and unmovable with respect to the probe wherein the transducer has at least one piezoelement capable of transmitting signals and receiving signals along the scanline;

ultrasound electronics in communication with the probe, the ultrasound electronics transmitting signals and receiving signals from the probe;

an electromagnetic positioning receiving sensor mechanically coupled to the probe;

an electromagnetic positioning transmitter for transmitting probing magnetic fields to the positioning receiving sensor, wherein the transmitter is stationary relative to the freehand probe;

means coupled to the electronics and the electromagnetic positioning receiving sensor for computing the spatial position and the orientation of at least one sampled scanline using position information from the sensor and transmitting the scanline orientation and spatial position to the electronics wherein the electronics identifies each scanline by a unique spatial address;

a memory coupled to the electronics for storing the addressed scanlines; and a display coupled to the memory and electronics for displaying the addressed scanlines wherein the movement of the probe results in the accumulation of multiple spatial addressed scanlines displayable as an image in a scanplane.

9. The device of claim 8, further comprising a means for marking the location of the probe on the body being examined during examination.

10. The device of claim 8, wherein the ultrasonic transducer has at least one single concave piezoelement.

11. The device of claim 8, wherein the ultrasonic transducer has a circular piezoelement.

12. The device of claim 8, wherein the ultrasonic transducer is a multielement annular array.

13. A method of ultrasonically imaging a body, the method comprising the steps of:

providing an untethered ultrasound transducer having a scanline of fixed unmoving orientation relative to the transducer, the transducer having an integrated spatial position sensor;

placing the untethered ultrasound transducer on an exterior body surface of a patient;

operating the untethered transducer;

receiving at least one scanline of ultrasound data from the transducer;

addressing the at least one scanline with a spatial position and orientation of the transducer wherein the spatial position sensor provides the spatial position and orientation;

receiving a plurality of scanlines of ultrasound data from a plurality of transducer positions, addressing each scanline of ultrasound data with a unique spatial position and orientation and reporting the unique spatial positions and orientations to ultrasound electronics and display an image formed by the scanline; and displaying an image composed of multiple such scanlines as a two dimensional image.

14. The method of claim 13 further comprising the step of defining a nonplanar image slice of the body by a two dimensional image which is either planar or curved in at least one direction.

15. The device of claim 8, wherein the ultrasonic transducer has at least one single convex piezoelement.

16. The device of claim 15, wherein the piezoelement is circular in shape.

* * * * *

UNITED STATES PATENT AND TRADEMARK OFFICE
CERTIFICATE OF CORRECTION

PATENT NO. : 5,690,113
DATED : November 25, 1997
INVENTOR(S) : John W. Sliwa, Jr. et al.

It is certified that error appears in the above-identified patent and that said Letters Patent is hereby corrected as shown below:

In the Claims

In Claim 1, line 9, replace "electronic" with --electronics--.

In Claim 1, line 22, after "scanlines;" insert --and--.

In Claim 13, line 21, replace "scanline" with --scanlines--.

Signed and Sealed this

Sixth Day of July, 1999

Attest:

Q. TODD DICKINSON

*Attesting Officer*     *Acting Commissioner of Patents and Trademarks*